United States Patent [19]
Travis

[11] Patent Number: 5,276,432
[45] Date of Patent: Jan. 4, 1994

[54] PATIENT EXIT DETECTION MECHANISM FOR HOSPITAL BED

[75] Inventor: Stephen C. Travis, Paw Paw Township, Van Buren County, Mich.

[73] Assignee: Stryker Corporation, Kalamazoo, Mich.

[21] Appl. No.: 821,500

[22] Filed: Jan. 15, 1992

[51] Int. Cl.⁵ ................ G08B 23/00; G01M 1/12
[52] U.S. Cl. .................... 340/573; 73/65.01; 340/666
[58] Field of Search .............. 340/573, 666-; 200/85; 364/567; 128/774, 782, 714, 721; 73/65; 177/199-; 5/424

[56] References Cited

U.S. PATENT DOCUMENTS

| | | |
|---|---|---|
| 3,096,061 | 7/1963 | Bertell . |
| 3,217,818 | 11/1965 | Engelsher et al. . |
| 3,766,344 | 10/1973 | Nevett . |
| 3,876,018 | 4/1975 | Mracek et al. . |
| 3,890,958 | 6/1975 | Fister et al. ............ 73/65 X |
| 3,991,414 | 11/1976 | Moran . |
| 4,015,677 | 4/1977 | Silva et al. . |
| 4,020,482 | 4/1977 | Feldl . |
| 4,023,633 | 5/1977 | Swersey et al. . |
| 4,175,263 | 11/1979 | Triplett et al. . |
| 4,195,287 | 3/1980 | McCoy et al. . |
| 4,228,426 | 10/1980 | Roberts . |
| 4,242,672 | 12/1980 | Gault . |
| 4,295,133 | 10/1981 | Vance . |
| 4,363,368 | 12/1982 | Paddon et al. . |
| 4,539,560 | 9/1985 | Fleck et al. . |
| 4,550,793 | 11/1985 | Giles .................. 177/145 |
| 4,551,882 | 11/1985 | Swersey et al. . |
| 4,601,356 | 7/1986 | Muccillo, Jr. . |
| 4,633,237 | 12/1986 | Tucknott et al. ........... 340/573 |
| 4,751,754 | 6/1988 | Bailey et al. . |
| 4,805,637 | 2/1989 | Walthert .................. 128/774 |
| 4,934,468 | 6/1990 | Koerber, Sr. et al. . |
| 4,947,298 | 8/1990 | Stephen ............. 200/85 R X |
| 4,953,244 | 9/1990 | Koerber, Sr. et al. . |
| 4,961,470 | 10/1990 | Koerber, Sr. . |

Primary Examiner—John K. Peng
Assistant Examiner—Thomas J. Mullen, Jr.
Attorney, Agent, or Firm—Flynn, Thiel, Boutell & Tanis

[57] ABSTRACT

A hospital bed includes a support frame which is supported on the bed by four load cells and which in turn supports a mattress having a patient thereon. A method and apparatus of detecting patient exit from the bed involve extraction from the weight measured by each load cell of the portion of the measured weight corresponding to the weight of the patient, use of this extracted weight information to calculate a center of gravity of the patient with respect to the frame, a determination of whether the calculated center of gravity is within a predetermined region, and generation of an alarm if the center of gravity is outside the region.

18 Claims, 3 Drawing Sheets

PATIENT EXIT DETECTION MECHANISM FOR HOSPITAL BED

FIELD OF THE INVENTION

The present invention relates to an arrangement for detecting patient exit from a hospital bed and, more particularly, to an arrangement capable of detecting patient exit while a substantial portion of the patient's weight is still supported on the bed.

BACKGROUND OF THE INVENTION

In a hospital, it is sometimes necessary to monitor a patient in order to ensure that the patient remains in bed. For example, a patient who is physically capable of leaving the bed but who is subject to dizziness upon standing up might fall and injure himself if he leaves the bed when no attendant is present. Consequently, it is desirable that an alarm be given in the event the patient leaves the bed so that a member of the hospital staff will be alerted to the fact that the patient has left the bed and will ensure that the patient does not experience an injury.

An early technique for automatically detecting patient exit involved the provision of a normally-closed mechanical switch in the mattress or springs of a bed, the weight of the patient being sufficient to open the switch, and the absence of the patient permitting the switch to assume its closed condition. The switch could be connected in a series circuit with a source of power such as a battery and with an alarm such as a buzzer, and would thus produce audible noise when the patient left the bed.

Modern hospital beds typically have a supporting frame which supports the mattress and the patient, the supporting frame being itself supported on the bed by a plurality of load cells which each produce an electrical signal representative of the respective mass or weight supported by that load cell. In a conventional system of this type, the partial weight values from the various load cells can be periodically summed in order to produce a total weight value, and this value is monitored for a reduction which exceeds a predetermined limit value. If the total measured weight drops to a value below the limit value, it is interpreted to mean that the patient has substantially or completely exited the bed. One known system of this type is disclosed in Koerber, Sr. et al U.S. Pat. No. 4,934,468. While known systems of this type have been adequate for their intended purposes, they have not been satisfactory in all respects.

For example, a substantial portion of the weight of the patient must be removed from the patient supporting frame before the system is capable of determining that the patient is exiting the bed. In the case of a patient who is attempting to stand up, this means that the patient must be supporting a significant portion of his own weight on the floor before the system can detect that the patient is attempting to exit the bed. Thus, the patient will be substantially on his own feet and may be starting to experience a dizzy spell before any alarm is given, with the possibility that the patient may fall and injure himself before hospital personnel can reach him. It would be desirable to be able to detect the exit sooner, for example where the patient has moved himself to a sitting position on the edge of the bed but has not yet placed his feet on the floor and thus has all of his weight still supported by the patient supporting frame.

It is therefore an object of the present invention to provide a patient exit detection apparatus which is capable of accurately detecting patient exit while all or at least a substantial portion of the patient's weight is still supported by a patient supporting frame of the bed.

A further object is to provide such a system which does not require significantly more structure than existing systems and is thus cost-competitive with existing systems, and which in the case of a microprocessor-based bed can be implemented solely through a software change and can thus be easily retrofit into preexisting microprocessor-based beds.

SUMMARY OF THE INVENTION

The objects and purposes of the invention, including those set forth above, are met according to one form of the invention by providing an apparatus having a load supporting frame which is supported by a plurality of load cells, a first arrangement responsive to the load cells for determining with respect to the frame a location of a center of gravity of a load supported by the frame, and a second arrangement for determining whether the location of the center of gravity is within a predetermined region.

According to a different form of the invention, a hospital bed includes a patient support frame which is supported by a plurality of load cells, and a detecting arrangement responsive to the load cells for detecting a situation in which a patient is leaving the frame, the detecting arrangement determining a location with respect to the frame of a center of gravity of a patient supported on the frame and determining whether the location of the center of gravity is within a predetermined region.

A different form of the invention involves a method of detecting patient exit from a patient supporting frame which is part of a bed and is supported by a plurality of load cells, the method including the steps of using signals from the load cells to calculate a location with respect to the frame of a center of gravity of a patient supported by the frame, and determining whether the location of the center of gravity is within a predetermined region.

BRIEF DESCRIPTION OF THE DRAWINGS

A preferred embodiment of the present invention will be described in detail hereinafter with reference to the accompanying drawings, in which.

DETAILED DESCRIPTION

Figure 1:
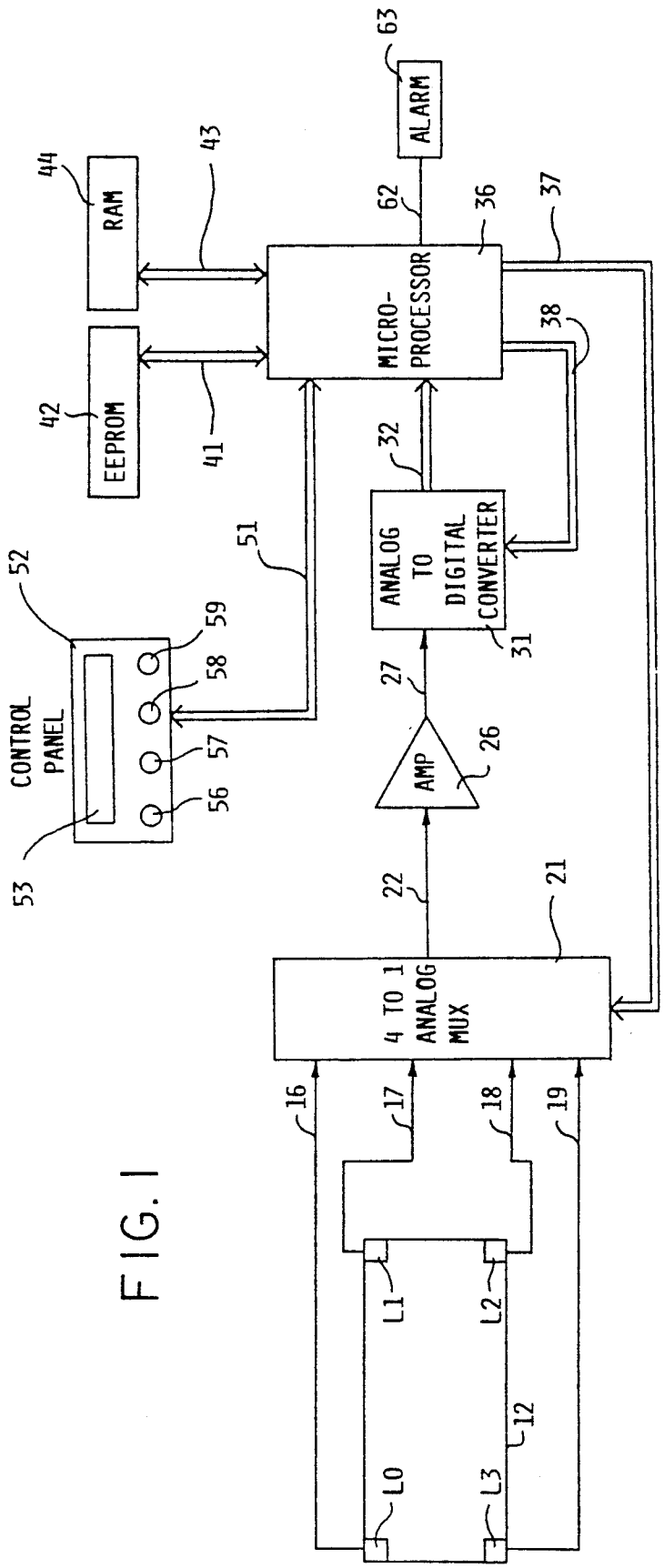
FIG. 1 is a block diagram of a patient exit detection system which embodies the present invention and is incorporated into a hospital bed.

Referring to FIG. 1, selected components of a hospital bed embodying the present invention are depicted. The bed includes a rectangular patient supporting frame, which is depicted diagrammatically at 12. The frame 12 is itself conventional and not a part of the present invention, and is therefore not described in detail. The frame 12 normally supports a not-illustrated mattress on which a hospital patient rests.

The frame 12 is supported in a conventional manner by four load cells L0–L3 which are each located at a respective corner of the frame 12. The load cells L0–L3 are conventional and commercially available parts with which persons skilled in this art are thoroughly familiar, and therefore are only briefly discussed here. In the preferred embodiment, the load cells L0–L3 each include a strain gauge in the form of a thick-film resistor, although it will be recognized that other conventional types of devices could also be utilized. In a conventional manner, the load cells L0–L3 not only support the frame, but each also produces an electrical signal representative of the weight which it is supporting, including the weight of the frame 12 and the weight of any mattress and patient supported on the frame.

The electrical signals produced by the load cells L0–L3 are supplied through respective wires 16–19 to four data inputs of a conventional and commercially available four-to-one analog multiplexer 21. The multiplexer 21 supplies to its output a selected one of the four analog signals present at its inputs, the output being connected at 22 to the input of a conventional analog amplifier 26. The output of the amplifier 26 is connected at 27 to the input of a conventional and commercially available analog-to-digital (A/D) converter 31, the digital outputs of which are connected at 32 to data inputs of a microprocessor 36.

The microprocessor 36 could be almost any conventional and commercially available microprocessor system. In the preferred embodiment, the microprocessor 36 is a MC68HC11 manufactured by Motorola of Schaumburg, Ill. The microprocessor has outputs which are connected by lines 38 to control inputs of the A/D converter 31, and has outputs which are connected at 37 to control inputs of the multiplexer 21.

The microprocessor 36 is also coupled at 41 to a conventional and commercially available electrically erasable programmable read only memory (EEPROM) 42, and is connected at 43 to a conventional and commercially available random access memory (RAM) 44. The EEPROM 42 stores values which do not change during normal system operation, whereas the RAM 44 stores values which may change during normal system operation. The values stored in each memory which are pertinent to the present invention will be discussed in more detail later. In the preferred embodiment, the RAM 44 is an integral part of the above-mentioned MC68HC11 integrated circuit which includes the microprocessor 36, but they are shown as separate blocks in the drawing for purposes of clarity.

The microprocessor 36 is coupled at 51 to a control panel 52, which has a conventional liquid crystal display (LCD) at 53 and has several manually operable push-button keys 56–59. The control panel 52 is of a type commonly found on modern hospital beds and is not in and of itself the focus of the present invention, and is therefore not described here in detail. The microprocessor 36 also has an output 62 controlling an alarm 63, which in FIG. 1 is a local alarm device such as a buzzer mounted on the bed. However, it will be recognized that the alarm 63 could alternatively be provided at a location remote from the bed.

Figure 2:
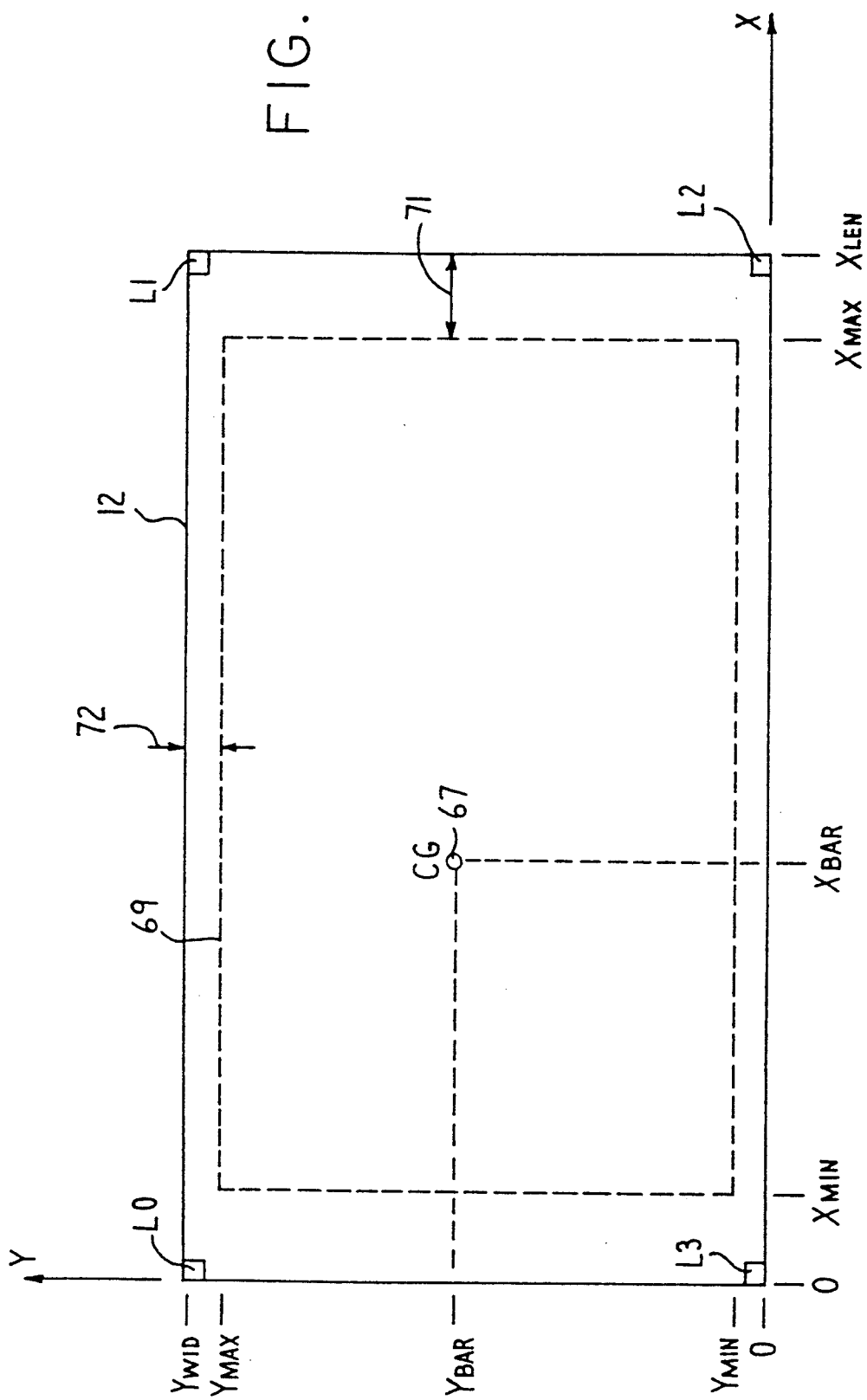
FIG. 2 is a diagram of a patient supporting frame and several load cells which are components of the system of FIG. 1, shown in reference to a two-dimensional Cartesian coordinate system.

FIG. 2 shows in a larger scale the bed frame 12 and the four load cells L0–L3. Since the load cells support the frame and also any loads which are in turn supported by the frame, including a patient, the total weight of the structure supported by the load cells can be obtained by summing the respective weight values measured by the four load cells. A known approach for detecting when a patient leaves or exits the bed is to simply look for a reduction in the total weight by an amount roughly equivalent to the weight of the patient. However, this approach normally requires that the patient in fact be almost completely off the bed before the total weight will drop to a point where the exit condition can be recognized. The present invention therefore takes a different approach, which has the advantage of being able to detect exit before the patient is substantially off the bed, and in some cases while the patient is still completely supported by the frame.

The basic approach according to the invention involves the concept of viewing the frame as disposed within a horizontal plane, extracting from the weight value measured by each load cell a portion which represents the weight of a patient, using the extracted portions to calculate the location within the plane of a center of gravity of the patient, determining whether the location of the center of gravity is inside or outside a predetermined region which is a portion of the plane, and initiating an alarm when it is found that the center of gravity is located outside the predetermined region.

In FIG. 2, a two-dimensional Cartesian coordinate system represents the horizontal plane and serves as a reference for calculating a center of gravity. The coordinate system has axes X and Y with an origin at the load cell L3, the axis X extending lengthwise of the frame along one side thereof and the axis Y extending transversely of the frame along one end thereof. The origin could alternatively be anywhere in the plane, and has been arbitrarily located at load cell L3 in the preferred embodiment.

With reference to FIG. 2, the Cartesian coordinates for the four load cells are $(0, Y_{WID})$ for L0, $(X_{LEN}, Y_{WID})$ for L1, $(X_{LEN}, 0)$ for L2, and $(0,0)$ for L3. $X_{LEN}$ and $Y_{WID}$ are respectively the dimensions in inches of the length and width of the frame 12, as defined by the distances between the load cells at its corners. A calculated center of gravity CG for a patient is shown diagrammatically at 67, and has Cartesian coordinates $(X_{BAR}, Y_{BAR})$. Of course, as the patient moves around, the location of the center of gravity will move with respect to the frame 12. As a patient attempts to exit the bed, or moves near the edge of the bed while sleeping, the periodically calculated center of gravity for the patient will move progressively toward an edge of the frame 12.

A broken line designates a rectangular region 69 within the horizontal plane. In the preferred embodiment, each end of the rectangular region 69 is spaced eight inches inwardly from a respective end of the frame 12, as shown diagrammatically at 71, and each side of the rectangular region 69 is spaced two inches inwardly from a respective side of the frame 12 as shown diagrammatically at 72. In the Cartesian coordinate system, the ends of the rectangular region bounded by line 69 are at $X_{MIN}$ and $X_{MAX}$ and the sides are at $Y_{MIN}$ and $Y_{MAX}$. If the calculated center of gravity for the patient is within the region 69, then no alarm is generated, but if the center of gravity moves outside the region 69 then the patient is assumed to be exiting the bed and an alarm is generated. Although the region 69 is rectangular in the preferred embodiment, it will be recognized that other shapes for the region are possible, and need not necessarily be regular geometric figures.

With reference to the coordinate system of FIG. 2, the location of the center of gravity 67 is determined by calculating its Cartesian coordinates ($X_{BAR}$, $Y_{BAR}$) according to the following equations:

$$X_{BAR} = \sum_{i=0}^{3} (M(i) \cdot X(i))/TM$$

$$Y_{BAR} = \sum_{i=0}^{3} (M(i) \cdot Y(i))/TM$$

$$TM = \sum_{i=0}^{3} M(i)$$

where X(i) is the abscissa of load cell Li for i=0 to 3, Y(i) is the ordinate of load cell Li, and M(i) is the portion of the mass or weight measured by load cell Li which corresponds to the weight of the patient.

Figure 3:
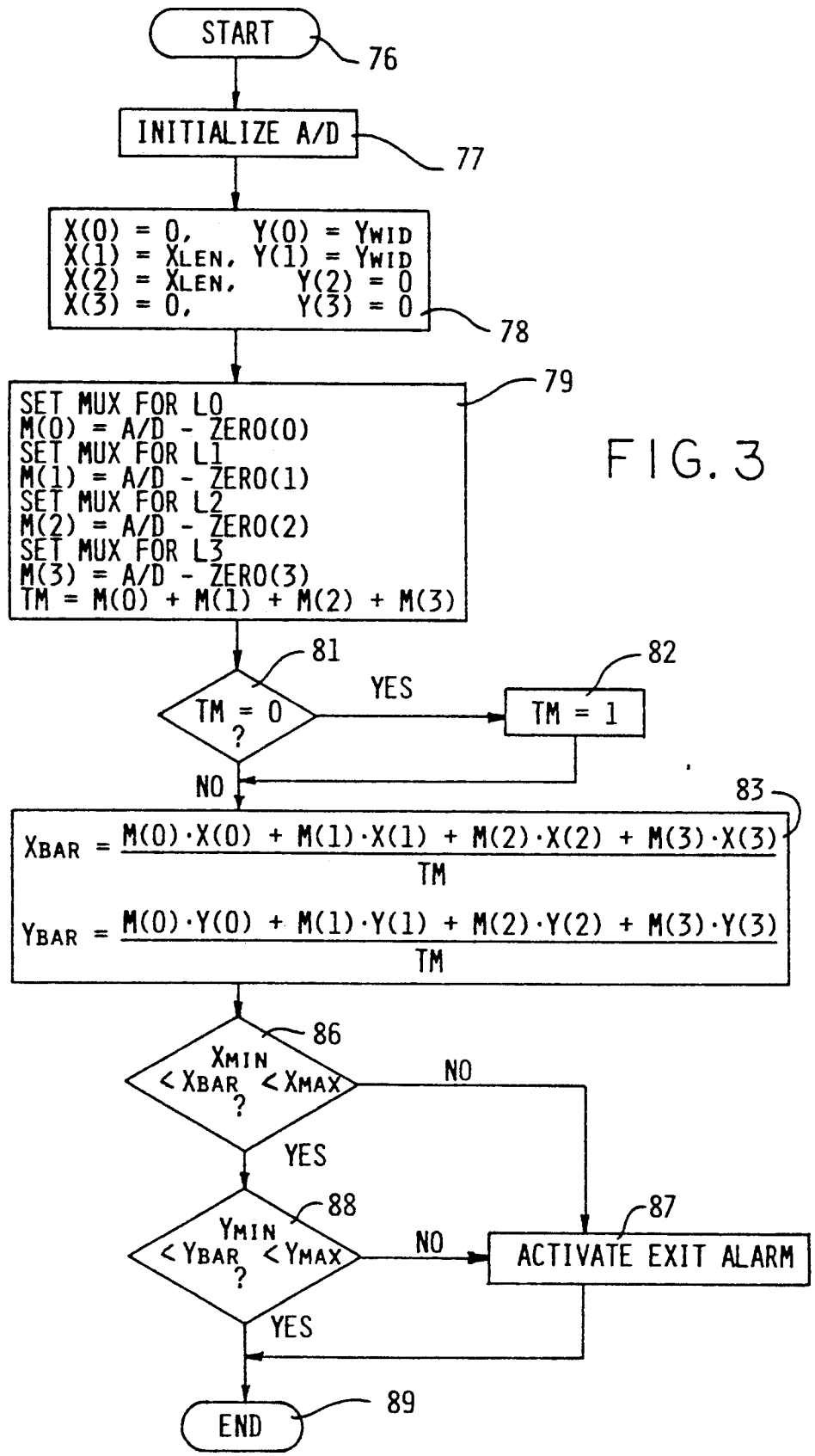
FIG. 3 is a flowchart of a software routine executed by a microprocessor which is a component of the system of FIG. 1.

The flowchart of FIG. 3 represents a routine which is part of the software program executed by the microprocessor 36 of FIG. 1, and in particular is a routine which is periodically executed when patient exit detection is enabled and which calculates the center of gravity of the patient using the foregoing equations and then determines whether the calculated center of gravity is located within the rectangular region 69.

As mentioned above, the EEPROM stores values which do not normally change during system operation. More specifically, the EEPROM 42 stores $X_{LEN}$, $Y_{WID}$, $X_{MAX}$, $X_{MIN}$, $Y_{MAX}$ and $Y_{MIN}$, which are constants corresponding to respective distances along the X and Y axes as shown in FIG. 2. In addition, the EEPROM stores values ZERO(0) to ZERO(3), which are values corresponding to the respective masses or weights measured by the respective load cells L0-L3 when there is no patient on the bed, or in other words the tare weight at each load cell.

As also mentioned above, the RAM 44 stores variable values which may change dynamically during normal system operation. In particular, the RAM 44 includes a one-dimensional array with four elements X(0)-X(3) which contain the abscissas of the respective load cells L0-L3, a one-dimensional array having four elements Y(0)-Y(3) which contain the ordinates of the respective load cells L0-L3, a one-dimensional array with four elements M(0)-M(3) which contain the portions of the mass or weight measured by the respective load cells L0-L3 and corresponding to patient weight, a variable TM which contains the sum of the four values in M(0)-M(3), and variables $X_{BAR}$ and $Y_{BAR}$ which respectively contain the abscissa and ordinate of the calculated center of gravity.

Execution of the routine of FIG. 3 begins at block 76, and proceeds to block 77, where the microprocessor 36 uses the control lines 38 to initialize the A/D converter 31. Those of ordinary skill in the art are thoroughly familiar with the techniques involved in initializing an A/D converter, and these techniques are therefore not described in detail here.

Control then proceeds to block 78, where the array elements X(0)-X(3) and Y(0)-Y(3) are initialized using the values $X_{LEN}$ and $Y_{WID}$ from the EEPROM, in particular so that (X(i), Y(i)) contain the Cartesian coordinates of load sensor Li where i=0 to 3.

Then, at block 79, the microprocessor 36 sets lines 37 so as to cause the multiplexer 21 to supply the signal on line 16 from load cell L0 to its output 22, this analog signal being amplified by amplifier 26 and supplied to the A/D converter 31, which then produces at 32 a digital value representative of the total mass or weight measured by load cell L0. Next, still in block 79, the microprocessor takes this value from the A/D converter and subtracts from it the value ZERO(0) stored in EEPROM 42, in order to eliminate the effect of the tare weight and thus leave only the measured mass or weight corresponding to a patient, which is then stored in array element M(0). In block 79, this sequence is repeated for each of the other three load cells L1-L3. Then the values stored in the array elements M(0)-M(3) are added together in order to obtain the total mass or weight of the patient, and the result is stored in variable TM in the RAM 44.

Control then proceeds to block 81, where the microprocessor checks to see if the variable TM in the RAM 44 contains a value of 0, which only occurs where the array elements M(0) through M(3) are all zero because there is no patient on the bed. If TM is 0, then control proceeds to block 82, where TM is forced to a value of 1 so that the subsequent use of TM as a divisor will not result in division by zero, which of course is impossible and would cause the microprocessor 36 to flag an error.

From blocks 81 and 82, control ultimately proceeds to block 83, where $X_{BAR}$ and $Y_{BAR}$ are calculated according to the equations set forth above. It should also be noted that, if TM was set to a value of 1 in block 82 in order to avoid division by 0 in block 83, it will not affect the accuracy of the calculation in block 83. In particular, the array elements M(0)-M(3) will necessarily each be equal to zero, and will thus force the numerator of each calculation in block 83 to zero so that $X_{BAR}$ and $Y_{BAR}$ are each set to zero. Thus, when there is no patient on the bed and M(0)-M(3) are all zero, the calculated coordinates of the center of gravity 67 (FIG. 2) will be at the origin (0,0) of the coordinate system, which is a point outside the boundary 69 and which will thus properly initiate an alarm because it represents a situation in which the patient has exited the bed.

From block 83, control proceeds to block 86, where the microprocessor checks to see if the calculated abscissa $X_{BAR}$ for the center of gravity is between the ends $X_{MIN}$ and $X_{MAX}$ of the rectangular region 69 in FIG. 2. If it is not, or in other words if the location of the center of gravity is to the left of the line $X_{MIN}$ or to the right of the line $X_{MAX}$, then the microprocessor concludes that the patient has exited the bed or is about to exit the bed, and proceeds to block 86 where it uses output line 62 (FIG. 1) to activate the alarm 63. On the other hand, if it is determined at block 86 that the abscissa $X_{BAR}$ of the center of gravity is within the region 69, then control proceeds to block 88, where the microprocessor checks to see if the ordinate $Y_{BAR}$ of the center of gravity is between the sides $Y_{MIN}$ and $Y_{MAX}$ of the rectangular region 69. If it is, then blocks 86 and 88 have together determined that the center of gravity is within the rectangular region 69, in which case no alarm is raised and control proceeds to block 89 where the routine ends. On the other hand, if it is determined at block 88 that the ordinate $Y_{BAR}$ is outside either limit, and thus necessarily outside the rectangular area 69 in FIG. 2, control proceeds to block 87, where an alarm is generated. From block 87, control proceeds to block 89, where the routine ends.

As discussed above, the values stored in the EEPROM 42 do not change during normal system operation. However, it may from time to time be necessary to update the values ZERO(0)-ZERO(3) which contain the tare values for the respective load cells. For example, if an additional structural component such as an IV pole is mounted on the frame 12 of the bed, the tare weight readings stored in the EEPROM will need to be updated to reflect the weight of the IV pole. In the preferred embodiment, this is effected by pressing one or more of the buttons 56-59 on the control panel 52 in a predetermined sequence, causing the microprocessor 36 to execute a special routine in which, with no patient on the bed, the multiplexer 21 is controlled to successively select each of the four load cells L0-L3, and the output 32 from the A/D converter 31 for each load cell is read into the microprocessor 36 and stored in a corresponding one of the locations ZERO(0)-ZERO(3) of the EEPROM 42. In essence, this constitutes calibration of the disclosed apparatus so that the location of the center of gravity can be accurately calculated when a patient is in fact later present on the bed. This calibration by updating of the tare values in ZERO(0)-ZERO(3) is conventional and not in and of itself a feature of the present invention, and has therefore been described only briefly in order to facilitate an understanding of the present invention.

So far, the foregoing discussion has assumed that the strain gauges used for the load cells L0-L3 all have electrical gains which are equal. In reality, there will typically be some variations in the gains of respective load cells. For purposes of detecting patient exit according to the present invention, it has been found that typical variations in the gains of available strain gauges have a negligible effect on the accuracy of the calculation of the location of the center of gravity. Therefore, the preferred embodiment does not attempt to normalize the readings obtained from the respective load cells before calculating the center of gravity. Nevertheless, the present invention encompasses a situation in which the outputs of the load cells are normalized. One conventional approach for effecting normalization is to provide a circuit at each load cell which has an adjustable rheostat used as a trimming component to adjust the magnitude of the output signal of the load cell so the four signals 16-19 supplied to the inputs of the multiplexer 21 are effectively normalized with respect to each other. A less expensive approach is to directly connect the strain gauges to the multiplexer 21 with no additional circuitry (as in the preferred embodiment), to store in the EEPROM a respective compensation coefficient for each load cell, and to have the microprocessor multiply each value received from the A/D converter 31 by a respective one of the four compensation coefficients corresponding to the particular load cell currently selected by the multiplexer 21. Both of these normalization approaches are, in and of themselves, entirely conventional. While the present invention can provide accurate results without the use of normalization, the present invention is also compatible with and encompasses the use of normalization, including normalization by these two known approaches.

Although a single preferred embodiment of the invention has been illustrated and described in detail, it will be recognized that there are variations of the disclosed embodiment which lie within the scope of the present invention.

The embodiments of the invention in which an exclusive property or privilege is claimed are defined as follows:

1. An apparatus comprising: a load supporting frame which is supported by a plurality of spaced load cells first means responsive to said load cells for determining a location on said frame of the center of gravity of a load supported by said frame, and second means for determining whether said location of said center of gravity is within a predetermined region.

2. An apparatus according to claim 1, wherein said first means periodically effects said determination of said location of said center of gravity, and said second means periodically effects said determination of whether said location is within said predetermined region.

3. An apparatus according to claim 1, including third means responsive to said second means for generating an alarm in response to a determination by said second means that said location of said center of gravity is outside said predetermined region.

4. An apparatus according to claim 1, wherein said frame is approximately rectangular, and wherein there are four of said load cells each disposed in the region of a respective corner of said frame.

5. An apparatus according to claim 4, wherein said first means determines said location of said center of gravity as a point having coordinates ($X_{BAR}$, $Y_{BAR}$) within a two-dimensional Cartesian coordinate system having two horizontally extending X and Y axes, according to the following equations:

$$X_{BAR} = \sum_{i=0}^{3} (M(i) \cdot X(i))/TM$$

$$Y_{BAR} = \sum_{i=0}^{3} (M(i) \cdot Y(i))/TM$$

$$TM = \sum_{i=0}^{3} M(i)$$

where each value of i represents a respective said load cell, X(i) and Y(i) are respectively the abscissa and ordinate for a respective load cell, and M(i) is a portion of the weight of the load on the frame measured by a respective said load cell.

6. An apparatus according to claim 5, wherein the values M(i) each represent a current measured output value from a respective said load cell less a respective predetermined tare value for that load cell.

7. An apparatus according to claim 6, wherein each said current measured value and each said tare value is a direct reading from a respective said load cell which is uncompensated for gain variations between said load cells.

8. An apparatus according to claim 4, wherein said predetermined region is a generally rectangular region shorter in length and in width than said rectangular frame, the edges of said rectangular region each being substantially parallel to and spaced inwardly from a respective edge of said rectangular frame.

9. In a hospital bed which includes a patient support frame supported by a plurality of spaced load cells, and detecting means coupled to said load cells and responsive to physical movement relative to said frame of a patient supported by said frame for detecting the patient leaving the frame, the improvement comprising said detecting means having means for determining a location on said frame of the center of gravity of a patient supported by said frame and for determining whether said location of said center of gravity is within a predetermined region.

10. A bed according to claim 9, wherein said patient support frame has a length in a first direction which is greater than a width in a second direction perpendicular to said first direction, wherein said detecting means determines said location of said center of gravity with respect to said frame in a direction substantially parallel to said second direction, and wherein said predetermined region is disposed between first and second limits which are spaced from each other in said second direction.

11. A bed according to claim 10, wherein said detecting means also determines said location of said center of gravity with respect to said frame in a direction substantially parallel to said first direction, and wherein said predetermined region is disposed between third and fourth limits which are spaced from each other in said first direction.

12. A method of detecting patient exit from a patient supporting frame which is part of a bed and is supported by a plurality of spaced load cells, comprising the steps of: detecting physical movement relative to said frame of a patient supported by said frame by monitoring variation of a location on said frame of the center of gravity of the patient supported by said frame based on signals from said load cells, and determining whether said location of said center of gravity is within a predetermined region.

13. A method according to claim 12 further including the step of generating an alarm in response to a determination that said location of said center of gravity is outside said predetermined region.

14. A method according to claim 12, wherein said patient supporting frame has a length in a first direction which is greater than a width in a second direction perpendicular to said first direction, wherein said detecting step is carried out by determining said location of said center of gravity with respect to said frame along an axis substantially parallel to said second direction, and wherein said step of determining whether said location is within said predetermined region is carried out by using as said predetermined region a region between first and second limits which are spaced from each other in said second direction.

15. A method according to claim 14, wherein said detecting step is carried out by also determining said location of said center of gravity with respect to said frame along an axis substantially parallel to said first direction, said predetermined region extending between third and fourth limits spaced from each other in said first direction.

16. An apparatus comprising: a bed with a patient support section having a mattress which has substantially parallel side edges and an upwardly facing patient support surface extending between said side edges; load cell means cooperating with said patient support section to detect physical movement relative to said mattress of a patient supported by the mattress; first means responsive to said load cell means for determining a location, along an axis substantially perpendicular to said edges, of the center of gravity of the patient supported on the mattress; and second means responsive to said first means for determining whether said location is within a predetermined region, and for generating a signal serving as a warning of patient exit from the bed when said location is determined to be outside said predetermined region.

17. An apparatus according to claim 16, wherein the length of said patient support section in a direction substantially parallel to said side edges is greater than the distance between said side edges; and wherein said predetermined region is disposed between first and second limits which are spaced in a direction parallel to said axis.

18. An apparatus according to claim 16, wherein said load cell means includes a plurality of load cells provided at locations spaced from each other and collectively supporting said patient support section, and wherein said first means is responsive to said load cells for determining said location of said center of gravity along an axis substantially parallel to said side edges.

* * * * *